(12) United States Patent
Billodeaux et al.

(10) Patent No.: US 9,975,840 B2
(45) Date of Patent: May 22, 2018

(54) ALDEHYDE OXIDATION PROCESSES

(71) Applicant: Eastman Chemical Company, Kingsport, TN (US)

(72) Inventors: Damon Ray Billodeaux, Longview, TX (US); Kenneth Wayne Hampton, Jr., Gilmer, TX (US); Chad A. Johnson, Longview, TX (US)

(73) Assignee: Eastman Chemical Company, Kingsport, TN (US)

(*) Notice: Subject to any disclaimer, the term of this patent is extended or adjusted under 35 U.S.C. 154(b) by 0 days. days.

(21) Appl. No.: 15/215,206

(22) Filed: Jul. 20, 2016

(65) Prior Publication Data
US 2016/0326083 A1 Nov. 10, 2016

Related U.S. Application Data

(63) Continuation of application No. 14/568,667, filed on Dec. 12, 2014, now Pat. No. 9,428,435, which is a continuation-in-part of application No. 14/105,945, filed on Dec. 13, 2013, now Pat. No. 9,227,903.

(51) Int. Cl.
C07C 51/235 (2006.01)
C07C 51/16 (2006.01)
C07C 67/44 (2006.01)

(52) U.S. Cl.
CPC ............ C07C 51/235 (2013.01); C07C 51/16 (2013.01); C07C 67/44 (2013.01)

(58) Field of Classification Search
CPC .............................. C07C 51/235; C07C 51/16
USPC ....................................................... 562/531
See application file for complete search history.

(56) References Cited

U.S. PATENT DOCUMENTS

| 4,350,829 A | 9/1982 | Masuko et al. |
| 2006/0052633 A1 | 3/2006 | Lee et al. |

FOREIGN PATENT DOCUMENTS

| DE | 1 518 847 | 10/1969 | | |
| EP | 0 855 996 B1 | 1/2002 | | |
| EP | 0855996 B1 * | 1/2002 | ........... | C07C 51/235 |
| WO | WO 98/25876 A1 | 6/1998 | | |

OTHER PUBLICATIONS

Lehtinen, Christel et al.; "Experimental and computational studies on solvent effects in reactions of peracid-aldehyde adducts"; Tetrahedron; Mar. 2001; vol. 57, pp. 4741-4751.
Notification of Transmittal of the International Search Report and the Written Opinion of the International Searching Authority, or the Declaration dated Mar. 4, 2015 received in International Patent Application No. PCT/US2014/070047.

* cited by examiner

Primary Examiner — Craig D Ricci
Assistant Examiner — Janet L. Coppins
(74) Attorney, Agent, or Firm — James Arnold, Jr.

(57) ABSTRACT

The oxidation of isobutyraldehyde produces isobutyric acid and byproducts, such as isopropyl formate. A process of reducing the isopropyl formate byproduct and other byproducts in the oxidation of isobutyraldehyde is described. The process uses a carbonyl compound, such as acetone, to reduce byproduct levels in the resulting product. Process for use of static mixers in oxidation reactions of aldehydes are also provided.

9 Claims, 1 Drawing Sheet

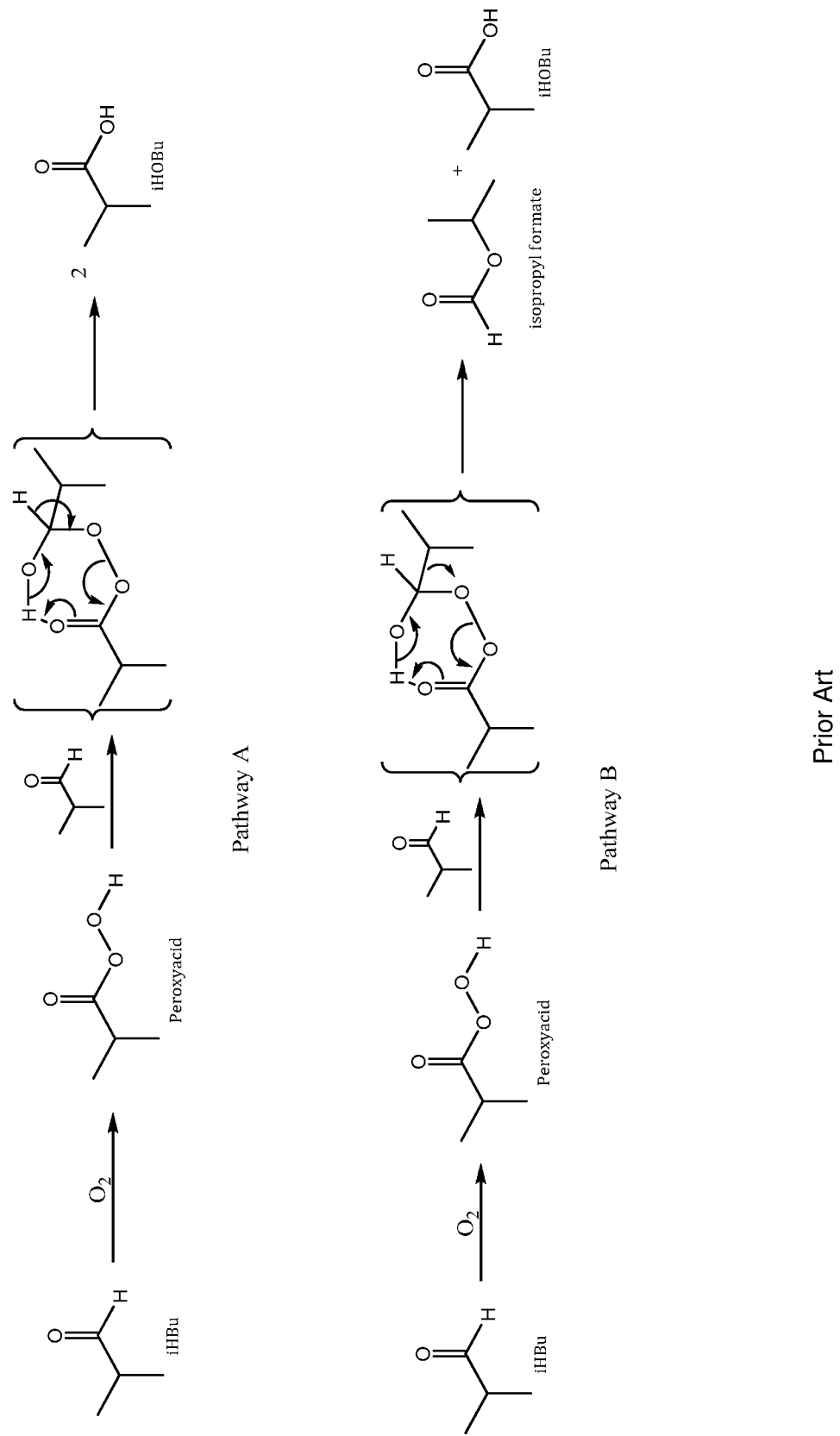

ALDEHYDE OXIDATION PROCESSES

CROSS-REFERENCE TO RELATED APPLICATIONS

This application is a continuation of U.S. patent application Ser. No. 14/568,667 filed Dec. 12, 2014 which is a continuation-in-part of U.S. patent application Ser. No. 14/105,945 filed on Dec. 13, 2013, the disclosures of which are incorporated herein by reference in its entirety.

BACKGROUND OF THE INVENTION

Isobutyric acid (iHOBu) has a number of commercial uses and is an intermediate in the manufacture of a number of esters and other compounds that have a variety of uses. A widely used way of making iHOBu is through the catalyzed or uncatalyzed oxidation of isobutyraldehyde (iHBu). Such oxidation processes have the problem of the formation of undesired byproducts. One such product is isopropyl formate (IPF). Some other examples of byproducts include carbon dioxide, isopropanol, propane, propylene and acetone.

While not wanting to be bound by a particular theory, it has been theorized that IPF is produced by the Baeyer-Villiger oxidation of isobutyraldehyde. This theorized mechanism is depicted in FIG. 1. According to this theory, the oxidation of the aldehyde results in the formation, first of peroxyacid, followed by the generation of an intermediate that can lead to production of two moles of the desired acid (Pathway A) or one mole of the desired acid and one mole of the undesired byproduct IPF (Pathway B). Pathway B is believed to result in the loss of some of the iHBu feed to form of the undesired byproduct IPF.

Formation of these byproducts consumes valuable raw materials and lowers the production of the desired acid. There are other drawbacks. For example, IPF byproduct is very difficult to separate from unreacted starting materials. Separated IPF from the crude product composition often includes unreacted isobutyraldehyde (iHBu) due to the proximity of their boiling points. Accordingly, the formation of IPF by-product is a significant financial burden on commercial production of isobutyric acid. Formation of non-IPF byproducts consumes raw materials and occupies volume in process equipment. It would therefore be beneficial to reduce or to eliminate formation of IPF in such processes.

BRIEF SUMMARY OF THE INVENTION

The invention provides methods for reducing byproduct formation is isobutyric acid formation. The invention provides processes that include:

feeding an oxidant, a carbonyl compound and a feed composition comprising isobutyraldehyde to a reaction zone; and withdrawing from the reaction zone a crude product composition comprising isobutyric acid and at least some of the carbonyl compound, wherein the carbonyl compound is selected from $C_3$-$C_8$ alkyl esters having no carbon chain exceeding four carbon atoms and $C_3$-$C_5$ alkyl ketones, and wherein the carbonyl compound is fed to the reaction zone in an amount sufficient to cause the crude product composition to comprise at least 5 weight percent of the carbonyl compound based on the total weight of the crude product composition. In some embodiments, the carbonyl compound is fed to the reaction zone in an amount sufficient to cause the crude product composition to comprise at least 5 weight percent of the carbonyl compound based on the total weight of the crude product composition.

The invention provides processes that include feeding an oxidant, a carbonyl compound and a feed composition comprising isobutyraldehyde to a reaction zone to form a crude product composition comprising isobutyric acid, wherein:

the carbonyl compound is selected from $C_3$-$C_8$ alkyl esters having no carbon chain exceeding four carbon atoms and $C_3$-$C_5$ alkyl ketones; and the carbonyl compound is fed to the reaction zone in an amount effective to reduce the formation of isopropyl formate compared with the production of isobutyric acid in the absence of the carbonyl compound.

In various embodiments of each of the above processes, the carbonyl compound is fed to the reaction zone in an amount sufficient to cause the crude product composition to comprise at least 6 percent, at least 7 percent, at least 8 percent, at least 9 percent, at least 10 percent, from 5 to 35 weight percent, from 7 to 35 weight percent, from 10 to 25 weight percent, or from 10 to 20 weight percent of the carbonyl compound based on the total weight of the crude product composition. In each of the processes and embodiments (including ranges) described above, the feed composition can be the result of combining at least two isobutyraldehyde compositions that each comprise isobutyraldehyde.

In some embodiments of each of the above processes, the reaction zone has a residence time of less than 120 minutes. In various embodiments of each of the above processes, the reaction zone has a residence time of less than 110 minutes, less than 100 minutes, less than 90 minutes less than 75 minutes, less than 60 minutes, less than 45 minutes, less than 30 minutes, less than 25 minutes, less than 20 minutes, less than 15 minutes, less than 10 minutes, less than five minutes, from 0 to 5 minutes, from 0 to 10 minutes, from 1 to ten minutes, from 1 to 20 minutes, from 10 to 20 minutes, from 10 to 50 minutes, from 10 to 25 minutes, from 5 to 30 minutes, from 30 to 60 minutes, from 5 to 60 minutes, from 5 to 90 minutes, from 1 to 90 minutes, from 1 to 75 minutes, from 1 to 100 minutes, from 1 to 110 minutes or from 50 to 110 minutes.

In embodiments of each of the processes and embodiments (including ranges) described above, the two or more feed compositions are fed separately to the reaction zone.

In embodiments of each of the processes and embodiments (including ranges) described above, the process further comprises feeding an isobutyric acid containing composition to the reaction zone.

In embodiments of each of the processes and embodiments (including ranges) described above, the feed composition comprises at least some of the carbonyl compound.

In embodiments of each of the processes and embodiments (including ranges) described above, the carbonyl compound and the feed composition are fed separately to the reaction zone.

In embodiments of each of the processes and embodiments (including ranges) described above, feeding at least some of the recycle composition to the reaction zone includes combining at least some of the recycle composition into the feed composition before feeding the feed composition to the reaction zone.

In embodiments of each of the processes and embodiments (including ranges) described above, the carbonyl compound is selected from $C_3$-$C_4$ alkyl esters and $C_3$-$C_4$ alkyl ketones, selected from methyl acetate, ethyl acetate, methyl ethyl ketone and acetone, is ethyl acetate, or is acetone.

In embodiments of each of the processes and embodiments (including ranges) described above, where the carbonyl compound is acetone, at least some of the acetone is obtained as a byproduct from an isobutyraldehyde oxidation reaction.

In embodiments of each of the processes and embodiments (including ranges) described above, where the carbonyl compound is acetone, at least some of the acetone is derived from the crude product composition.

In embodiments of each of the processes and embodiments (including ranges) described above, the reaction zone comprises an oxidation catalyst.

In embodiments of each of the processes and embodiments (including ranges) described above, the formation of the isopropyl formate can be reduced by from 40% to 70% by weight compared with the production of isobutyric acid in the absence of the carbonyl compound.

In embodiments of each of the processes and embodiments (including ranges) described above, the process is carried out at a temperature of from 30 to 70° C. and pressure of from 30 to 70 psig.

In embodiments of each of the processes and embodiments (including ranges) described above, the reaction zone comprises a static mixer. Furthermore, provides processes that include contacting an aldehyde having the formula $R_1$—CHO with an oxidant in a reaction zone that includes a static mixer to produce a carboxylic acid having the formula $R_1$—C(O)OH wherein $R_1$ is a $C_1$ to $C_9$ group selected from alkyl, alkenyl, aralkyl, and alkaryl groups optionally having one or more ether, diether, or hydroxyl radical provided that the total number of carbons does not exceed 9.

DESCRIPTION OF THE DRAWINGS

FIG. 1 depicts the theorized Baeyer-Villger reaction.

DETAILED DESCRIPTION

Unless indicated to the contrary, the numerical parameters set forth in the following specification and attached claims can represent approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be from 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention represent approximations in some embodiments, the numerical values set forth in the specific examples are intended to be reported precisely in view of methods of measurement. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the denomination of process steps, ingredients, or other aspects of the information disclosed or claimed in the application with letters, numbers, or the like is a convenient means for identifying discrete activities or ingredients and the recited lettering can be arranged in any sequence, unless otherwise indicated.

As used herein, the singular forms "a", "an", and "the" include plural referents unless the context clearly dictates otherwise. Thus, even use of language such as "at least one" or "at least some" in one location is not intended to imply that other uses of "a", "an", and "the" excludes plural referents unless the context clearly dictates otherwise. Similarly, use of the language such as "at least some" in one location is not intended to imply that the absence of such language implies that "all" is intended, unless the context clearly dictates otherwise.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "alkyl" as used herein refers to a group containing one or more saturated carbons, such as methyl, ethyl, n-propyl, isopropyl, n-butyl, iso-butyl, tert-butyl and the like. Thus, an "alkyl ketone" refers to the structure R—C(O)—R' wherein R and R' are each groups containing one or more carbons in which all bonds between carbons are saturated. Thus, for example, the term "$C_3$ to $C_5$ alkyl ketones" means the structure R—C(O)—R' wherein R and R' are each groups containing one or more carbons in which all bonds between carbons are saturated and wherein the total number of carbons in the structure is 3, 4, or 5. Similarly, an "alkyl ester" refers to the structure $R_x$—C(O)O—$R_y$ wherein $R_x$ and $R_y$ are groups that each contain one or more carbons in which all bonds between carbons are saturated. "$C_3$-$C_8$ alkyl esters having no carbon chain exceeding four carbon atoms" refers to the structure $R_x$—C(O)O—$R_y$ wherein $R_x$ and $R_y$ are groups that each contain one or more (but no more than four) carbons in which all bonds between carbons are saturated, and wherein the total number of carbons in the structure is 3, 4, 5, 6, 7 or 8.

The term "non-IPF impurities" shall refer to other byproducts formed by the oxidation of isobutyraldehyde to isobutyric acid. These are carbon dioxide, isopropanol, acetone, propane and propylene, except that in embodiments in which the carbonyl compound using the claimed process is acetone, acetone will only be counted as a "non-IPF impurities" to the extent that it exceeds the amount fed to the reaction zone. Thus, for example, if, in a continuous process, 5 moles of acetone per hour are fed to the reaction zone and 7 moles of acetone per hour are withdrawn in the crude product composition, 2 moles of acetone per hour will be counted as part of the non-IPF impurities.

Unless the context clearly dictates otherwise, where the application refers to amounts of materials present in feed compositions, it should be noted that in embodiments that involve feeding multiple feed compositions to the reaction zone, the amounts in the feed compositions are aggregated.

Similarly, unless the context clearly dictates otherwise, where the application refers to amounts of materials present in crude product compositions, it should be noted that in embodiments that involve removal of multiple crude product compositions from the reaction zone, the amounts in the product compositions are aggregated.

The term "containment" means a structure that defines a substantially enclosed space in which a fluid may be stored or processed or through which a fluid may flow or be conveyed. By "substantially enclosed" it is meant that while the containment has openings through which material can enter or leave, movement of the fluid into or out of the space is otherwise restricted if such openings are closed, blocked or otherwise made unavailable for entry or exit. Some examples of containments include tubes, pipes, tanks, columns and other vessels.

The term "concentrate" in reference to a constituent of a composition processed in a particular process or process step, means processing in a manner that produces at least one resulting composition having a higher mole percent of the constituent as compared to the mole percentage in the composition prior to such processing. This often involves producing a second resulting composition having a lower mole percent of the constituent as compared to the composition before being processed in the process or process step. Concentrating may be accomplished, for example, by distillation, flash separation, extraction or phase separation, filtration, membrane separation and other processes.

As used throughout this application, "selectivity" for a particular product or byproduct refers to percent selectivity, and is defined by the following equation:

$$\% \text{ Selectivity} = \frac{(\text{Moles of product or byproduct}) \times 100\%}{\text{Moles of isobutyraldehyde converted}}$$

As used throughout this application, "yield" for a particular product or byproduct refers to percent yield and is defined by the following equation:

$$\% \text{ Yield} = \frac{(\text{Moles of product or byproduct}) \times 100\%}{\text{Moles of isobutyraldehyde fed}}$$

When determining selectivity and yield for a batch or semi-continuous process, the "Moles" used in the calculations above are based on the total number of moles of isobutyraldehyde fed to the process and total number of moles of the particular product or byproduct produced during a batch or semi-continuous run. When determining selectivity and yield for a continuous process, the "Moles" used in the calculation above are based on the total number of moles of isobutyraldehyde fed to the process over a unit of time and the total number of moles of the particular product or byproduct produced during the same unit of time.

Compounds to Reduce Byproduct Formation

The invention provides processes for producing isobutyric acid. In one aspect, the invention provides processes that comprising feeding an oxidant, a carbonyl compound and a feed composition comprising isobutyraldehyde to a reaction zone to form a crude product composition containing isobutyric acid and the carbonyl compound. The carbonyl compound is selected from $C_3$-$C_8$ alkyl esters having no carbon chain exceeding four carbon atoms and $C_3$-$C_5$ alkyl ketones. In some embodiments, the carbonyl compound is fed to the reaction zone in an amount sufficient to cause the crude product composition to comprise at least 5 weight percent of the carbonyl compound based on the total weight of the crude product composition. In some embodiments, the carbonyl compound is fed to the reaction zone in an amount sufficient to cause the crude product composition to comprise at least 7 weight percent of the carbonyl compound based on the total weight of the crude product composition. Embodiments also exist in which the foregoing amount is at least 6 weight percent, at least 8 weight percent, at least 9 weight percent, at least 10 weight percent, at least 12 weight percent, at least 15 weight percent, at least 17 weight percent and at least 20 weight percent. In some embodiments, two or more carbonyl compounds are fed to the reaction zone, wherein each carbonyl compound is selected from $C_3$-$C_8$ alkyl esters having no carbon chain exceeding four carbon atoms and $C_3$-$C_5$ alkyl ketones.

In some embodiments, the process reduces the formation of by-products in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 5% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 5% of the carbonyl compound based on the total weight of the crude product composition (or is not fed at all). In some embodiments, the process reduces the formation of by-products in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 7% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 7% of the carbonyl compound based on the total weight of the crude product composition (or is not fed at all). In some embodiments, the process reduces the formation of by-products in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 10% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 10% of the carbonyl compound based on the total weight of the crude product composition (or is not fed at all). In some embodiments, the process reduces the formation of byproducts in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 12% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 12% of the carbonyl compound based on the total weight of the crude product composition (or is not fed at all). In some embodiments, the process reduces the formation of byproducts in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 15% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 15% of the carbonyl compound based on the total weight of the crude product composition (or is not fed at all). In some embodiments, the process reduces the formation of byproducts in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 17% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 17% of the carbonyl compound based on the total weight of the crude product composition (or is not fed at all). In some embodiments, the process reduces the formation of byproducts in the oxidation of isobutyraldehyde by contacting the reactants with a carbonyl compound. Thus, in some embodiments, the process has a lower selectivity for isopropyl formate production compared with selectivity for isopropyl formate production if the carbonyl compound either is fed to the reaction zone in an amount insufficient to cause the crude product composition to contain at least 20% of the carbonyl compound based on the total weight of the crude product composition (or is not fed at all), and the process further has a lower selectivity for formation of non-IPF byproducts production compared with selectivity for non-IPF byproducts production if the carbonyl compound is fed to the reaction zone in an amount insufficient to cause the crude product composition to contain at least 20% of the carbonyl compound based on the total weight of the crude product composition (or is not fed at all).

In some embodiments a plurality of feed compositions comprising isobutyraldehyde can be fed to the reaction zone. Thus, in some embodiments the feed composition can be the product of combining at least two isobutyraldehyde compositions that each comprise isobutyraldehyde. The at least two isobutyraldehyde compositions that both comprise isobutyraldehyde can be combined into the feed composition before being fed to the reaction zone. Alternatively, two or more feed compositions comprising isobutyraldehyde can be fed separately to the reaction zone. By "fed separately," it is meant that they are both fed without being combined, for example by being fed through separate ports or openings, being fed at different times, or both. One or more additional compositions that do not contain isobutyraldehyde may also be combined with a feed composition, fed separately from any feed composition, or both.

The carbonyl compound is selected from $C_3$-$C_8$ alkyl esters having no carbon chain exceeding four carbon atoms and $C_3$-$C_5$ alkyl ketones. In some embodiments, the carbonyl compound is selected from $C_3$-$C_8$ alkyl esters having no carbon chain exceeding four carbon atoms. In some embodiments, the carbonyl compound is selected from $C_3$-$C_5$ alkyl ketones. In some embodiments, the carbonyl compound is selected from $C_3$-$C_5$ alkyl esters and $C_3$-$C_4$ alkyl ketones. In some embodiments, the carbonyl compound is selected from $C_3$-$C_5$ alkyl esters. In some embodiments, the carbonyl compound is selected from and $C_3$-$C_4$ alkyl ketones. In some embodiments, the carbonyl compound is selected from methyl acetate, ethyl acetate, methyl ethyl ketone and acetone. In some embodiments, the carbonyl compound is selected from methyl acetate, ethyl acetate and acetone. In some embodiments, the carbonyl compound is selected from methyl acetate and ethyl acetate. In some embodiments, the carbonyl compound is selected from methyl ethyl ketone and acetone. In some embodiments, the carbonyl compound is selected from acetone and ethyl acetate. In some embodiments, the carbonyl compound is acetone. In some embodiments, the carbonyl compound is ethyl acetate. Use of acetone has the additional advantage of using a carbonyl compound that is already present since it is a byproduct of isobutyric acid production.

The carbonyl compound may be obtained from any source, including carbonyl compounds available for purchase, carbonyl compounds produced as a product, carbonyl compounds that have been used in the process and is being recycled, carbonyl compound byproduct obtained from the process and carbonyl compound byproduct obtained from another process. In some embodiments in which the carbonyl compound is acetone, at least some of the acetone can be a byproduct from an isobutyraldehyde oxidation reaction. The isobutyraldehyde oxidation reaction may be the process of the claimed invention or a different process. For example, the acetone may be derived from crude product composition.

In some embodiments, at least 20% of the carbonyl compound fed to the reaction zone has been derived from the crude product composition and recycled. In some embodiments, this amount is at least 25%, at least 30%, at least 40%, at least 50%, at least 60%, at least 70%, at least 80%, at least 90% or at least 95%. The amount may be also viewed as a range, such as from 25 to 50%, from 30 to 50%, from 40 to 50%, from 50 to 60%, from 50 to 75%, from 60 to 75%, from 70 to 80%, from 80 to 90%, from 75 to 95%, from 80 to 100%, from 90 to 100% m or from 75 to 100%. The foregoing percentages are by weight based on the total acetone fed to the reaction zone.

Adding additional materials to a feed in a process will often decrease the yield of the final product. It has been found that in some embodiments, despite a decrease in concentration of isobutyraldehyde feed, the overall production rate of isobutyric acid when the carbonyl compound is used is almost the same or even higher comparing to the process in which no carbonyl compound is used.

The carbonyl compound may be fed to the process or the reaction zone by being combined with one or more feed composition comprising isobutyraldehyde, fed separately, or fed as part of another composition.

In some embodiments, one or more isobutyric acid containing composition may be fed to the reaction zone. In some embodiments, the isobutyric acid containing composition is obtained from a downstream process step and recycled. Some examples include isobutyric acid product compositions, isobutyric acid containing scrubbants used to scrub process gases, compositions obtained from separation processes used downstream. Optionally, the isobutyric acid containing composition is cooled to remove at least some process heat before being fed to the reaction zone.

Other compounds and compositions may also be fed to or present in the reaction zone. Any other acceptable compounds and compositions may be present. For example, in some embodiments, a solvent is present and the carbonyl compound may for convenience be referred to as a co-solvent. In some embodiments, isobutyric acid, water, or a saturated hydrocarbon is present in the reaction zone as a solvent. Some examples of saturated hydrocarbons include hexane, pentane, heptane, octane and the like. Multiple solvents may be present. The solvent or solvents may be part of a feed to the process or to the reaction zone, may form in situ or both. For example, in some embodiments, isobutyric acid is present as a solvent, either as a product of the oxidation reaction, as a component of the feed or both. In some embodiments, an isobutyric acid containing composition of the type described above may provide the isobutyric acid solvent.

Thus, according to some embodiments, the invention provides processes for reducing isopropyl formate in a process of producing isobutyric acid comprising contacting isobutyraldehyde, a solvent and a co-solvent in the presence of an oxidant to form isobutyric acid, wherein the formation of isopropyl formate is reduced comparing with the production of isobutyric acid in the absence of a co-solvent. In such an embodiment, the carbonyl compound describe above may be seen as the co-solvent.

In embodiments of each of the above inventions, the amount of isopropyl formate byproduct produced is reduced, by 20% to 50% by weight, by 20% to 50% by weight, by 30% to 60% by weight, by 30% to 95.5% by weight, by 30% to 40% by weight, by 30% to 70% by weight, by 40% to 60% by weight, by 40% to 80% by weight, by 50% to 80% by weight, by 60% to 80% by weight, or 80% to 95.5% by weight, or by at least 95% by weight. The foregoing percentages refer to the isopropyl formate compared to the amount of isopropyl formate produced in the absence of the carbonyl compound, and can be determined using yield. Embodiments also exist in which the foregoing percentages refer to the isopropyl formate as compared to the amount of isopropyl formate produced if the carbonyl compound is fed in amounts insufficient to cause the crude product composition to comprise at least 10 weight percent of the carbonyl compound based on the total weight of the crude product composition. Embodiments also exist in which the foregoing percentages refer to the isopropyl formate as compared to the amount of isopropyl formate produced if the carbonyl compound is fed in amounts insufficient to cause the crude product composition to comprise at least 7 weight percent of the carbonyl compound based on the total weight of the crude product composition. Embodiments also exist in which the foregoing percentages refer to the isopropyl formate as compared to the amount of isopropyl formate produced if the carbonyl compound is fed in amounts insufficient to cause the crude product composition to comprise at least 5 weight percent of the carbonyl compound based on the total weight of the crude product composition.

The carbonyl compound may be present in the crude product composition in any effective percentage. In embodiments of the invention, the carbonyl compound is present in the amount of from 1 to 51 weight % based on the total weight of crude product composition. Embodiments exist in which this percentage is from 5 to 50 weight %, from 10 to 25 weight %, from 2.5 to 50 weight %, from 5 to 50 weight %, from 2.5 to 20 weight %, from 2.5 to 25 weight %, from 2.5 to 10 weight %, from 2.5 to 15 weight %, from 2.5 to 30 weight %, from 2.5 to 25 weight %, from 10 to 25 weight %, from 10 to 20 weight %, from 10 to 35 weight %, from 10 to 50 weight %, from 5 to 15 weight %, from 5 to 20 weight %, from 5 to 25 weight %, from 5 to 35 weight %, or from 10 to 35 weight %, with each of the forgoing percentages being based on the total weight of crude product composition. The term "reaction solution" as used herein has the same meaning as the crude product composition. As such the reaction solution may contain the same percentages.

The amount of carbonyl compound may also be described in relation to the amount of materials fed to the reaction zone. Thus, in some embodiments the carbonyl compound is fed in an amount sufficient to cause the crude product composition to comprise 1 to 51 weight percent of the carbonyl compound based on the total weight of the crude product composition. the carbonyl compound is fed in an amount sufficient to cause the crude product composition to comprise 2.5 to 50 weight %, from 5 to 50 weight %, from 2.5 to 20 weight %, from 2.5 to 25 weight %, from 2.5 to 10 weight %, from 2.5 to 15 weight %, from 2.5 to 30 weight %, from 2.5 to 25 weight %, from 10 to 25 weight %, from 10 to 20 weight %, from 10 to 35 weight %, from 10 to 50 weight %, from 5 to 15 weight %, from 5 to 20 weight %, from 5 to 25 weight %, from 5 to 35 weight %, from 1 to 51 weight % or from 10 to 35 weight percent of the carbonyl compound based on the total weight of the crude product composition.

The amount of carbonyl compound may also be described in relation to the amount of materials fed to the reaction zone. In some embodiments, the carbonyl compound is fed to the reaction zone at a rate that is at least 50 weight percent of the feed rate of isobutyraldehyde to the reaction zone. In some embodiments, the carbonyl compound is fed to reaction zone at a rate that is at least 50 weight percent, at least 75 weight percent, at least 100 weight percent, at least 150 weight percent, at least 200 weight percent, at least 250 weight percent, at least 300 weight percent or at least 500 weight percent of the feed rate of isobutyraldehyde to the reaction zone. In some embodiments, the carbonyl compound is fed to the reaction zone at a rate that is from 50 to 75, from 50 to 150, from 75 to 100, from 75 to 150, from 75 to 200, from 75 to 300, from 100 to 150, from 100 to 150, from 100 to 400, from 100 to 350, from 100 to 200, from 150 to 400, from 75 to 500, from 100 to 500, from 200 to 500 or from 300 to 500 weight percent of the feed rate of isobutyraldehyde to the reaction zone.

The process of producing isobutyric acid involving the oxidation (such as liquid phase oxidation) of isobutyraldehyde, can be carried out in the presence or absence of a catalyst. Optionally, acceptable catalysts such as, noble metal or transition metal salts can be used. Salts of cobalt, chromium, or manganese can also be useful for catalyzed oxidation of isobutyric acid. In many cases, uncatalyzed oxidation of isobutyric acid is just as or more effective than catalyzed oxidation.

The process according to each of the above embodiments can be carried out at any effective temperatures in the reaction zone. Some examples include from 0° C. to 100° C., from 20° C. to 70° C., from 25° C. to 50° C., from 30° C. to 70° C., from 30° C. to 60° C., from 40° C. to 60° C., from 30° C. to 50° C., from 50° C. to 70° C., from 40° C. to 50° C., from 50° C. to 60° C., or from 35° C. to 45° C., The process may be run at any effective ambient pressure in the reaction zone. Some examples include from ambient pressure to 200 pounds per square inch gage (psig), from 20 psig to 60 psig, from 40 psig to 50 psig, from 30 psig to 50 psig, from 50 psig to 60 psig, 3 from 0 psig to 60 psig, from 50 psig to 100 psig, from 50 psig to 150 psig, from 50 psig to 100 psig, from 100 psig to 150 psig, from 75 psig to 100 psig, from 90 psig to 130 psig, from 80 psig to 130 psig, from 90 psig to 125 psig, from 20 psig to 70 psig, or from 40 psig to 55 psig. Each combination of the foregoing temperatures and pressures is within the present invention.

Any suitable oxidant can be used in each of the embodiments described above to effect the transformation of isobutyraldehyde to isobutyric acid. Examples of such oxidants include gas mixtures containing oxygen (e.g. air) and pure oxygen or gas containing oxygen above 90% by weight. Liquid oxidants such as solutions of sodium hypochlorite and hydrogen peroxide can also be used. In embodiments in which a gas containing oxygen is used, it may be desirable to feed an inert gas such as nitrogen to the reaction zone as necessary to avoid oxygen levels reaching a level that will cause combustion. In some embodiments, the gas containing oxygen is ambient air, thus avoiding the costs of acquiring or generating enhanced or specialized gasses.

Each of the above processes described above can be conducted under continuous, semi-continuous, and batch modes of operation and can utilize a variety of reactor types. By "continuous" it is meant that the process is substantially or completely continuous in operation and is to be contrasted with a "batch" process. "Continuous" is not meant in any way to prohibit normal interruptions in the continuity of the process due to, for example, start-up, equipment maintenance, or scheduled shut down periods. The term "batch" process as used herein means a process wherein all the reactants are added to the reaction zone and then processed according to a predetermined course of reaction during which no material is fed or removed into the reactor. The term "semicontinuous" means a process where some of the reactants are charged at the beginning of the process and the remaining reactants are fed continuously as the reaction progresses to completion. Alternatively, a semicontinuous process may also include a process similar to a batch process in which all the reactants are added at the beginning of the process except that one or more of the products are removed continuously as the reaction progresses.

The invention confers the benefit of allowing reduction of byproduct formation even with shorter residence times in the reaction zone. In some embodiments the reaction zone has a residence time of less than 120 minutes. In some embodiments, the reaction zone has a residence time of less than 110 minutes, less than 100 minutes, less than 90 minutes less than 75 minutes, less than 60 minutes, less than 45 minutes, less than 30 minutes, less than 25 minutes, less than 20 minutes, less than 15 minutes, less than 10 minutes, less than five minutes, from 0 to 5 minutes, from 0 to 10 minutes, from 1 to ten minutes, from 1 to 20 minutes, from 10 to 20 minutes, from 10 to 50 minutes, from 10 to 25 minutes, from 5 to 30 minutes, from 30 to 60 minutes, from 5 to 60 minutes, from 5 to 90 minutes, from 1 to 90 minutes, from 1 to 75 minutes, from 1 to 100 minutes, from 1 to 110 minutes or from 50 to 110 minutes. As used herein, "residence time" shall refer to the time the liquid materials are contained within the reaction zone, as determined by dividing the volume of free space (i.e. space not occupied by gas, internals, packing, or other solids) in the reaction zone by the sum of the volumetric feed rates of all materials fed to the reaction zone.

Reactor Configurations

Any effective reactor designs or configurations may be used in carrying out the process provided by the present invention. Some examples of suitable reactor types include stirred tank, continuous stirred tank, tower, plug flow reactor, bubble column, heated tube type reactor and tubular reactor. The process also may be practiced in a batchwise manner by contacting the low molecular weight alcohol, hydrogen and carbon monoxide with the present catalyst composition in an autoclave. Thus, in some embodiments, the reaction zone is selected from one of the foregoing reactor types. Embodiments exist of each such type. In some embodiments, the reaction zone is a bubble column. In some embodiments, the reaction zone is a continuous stirred tank reactor.

Because oxidation involves the blending of a feed composition with an oxidant, efficient mixing will be conducive to intimate contact between the reactants and thus will be beneficial. It has also been found that adequate mixing can be accomplished in through the use of a static mixer. This is advantageous because static mixers are relatively inexpensive and allow for reduction in capital and maintenance costs. Thus, in some embodiments, the reaction zone is a static mixer.

Furthermore, an additional aspect of the invention is the use of static mixtures in an oxidation of an aldehyde to a carboxylic acid. The invention thus provides processes that include contacting an aldehyde with an oxidant in a reaction zone that includes a static mixer to produce a carboxylic acid. In some embodiments, the feed includes a carbonyl compound that is present in the reaction zone in an amount of between 5 and 50 weight percent based on the total mass of isobutyraldehyde fed to the reaction zone. This process may be used with all of the embodiments and ranges described in this application and all combinations of such embodiments and ranges. However, this aspect of the invention is not limited to embodiments that include the carbonyl compounds of the invention and embodiments exist in which the carbonyl compounds are absent or are present in amounts below 7%, below 5%, below 2.5%, or below 1% based on the total combined weight of the feed composition and the carbonyl compound (if any) fed to the reaction zone. Embodiments of this aspect of the invention exist using the examples and ranges of oxidants, temperatures, number of types of feed compositions, and other process variables discussed in the preceding sections, and all possible combinations thereof. Embodiments also exist that involve both the use of a static mixer reaction zone along with the carbonyl compound described above as well as all of the possible combinations of examples and ranges of oxidants, temperatures, number of types of feed compositions, and other process variables discussed in the preceding sections, and all possible combinations thereof.

This aspect of the invention is not limited to the oxidation of isobutyraldehyde to isobutyric acid. Thus, the invention provides processes that include contacting an aldehyde having the formula $R_1$—CHO with an oxidant in a reaction zone that includes a static mixer to produce a carboxylic acid having the formula $R_1$—C(O)OH wherein $R_1$ is a $C_1$ to $C_9$ group selected from alkyl, alkenyl, aralkyl, and alkaryl groups, optionally having one or more ether, diether, or hydroxyl radical provided that the total number of carbons does not exceed 9. In some embodiments, $R_1$ is selected from $C_1$ to $C_9$ alkyl and alkenyl groups optionally having one or more ether, diether, or hydroxyl radical. In some embodiments, $R_1$ is selected from $C_1$ to $C_9$ alkyl and alkenyl groups. In some embodiments, $R_1$ is selected from $C_1$ to $C_9$ alkyl groups. In some embodiments, $R_1$ is selected from $C_3$ to $C_8$ alkyl groups. In some embodiments, $R_1$ is selected from $C_3$ to $C_8$ alkyl and alkenyl groups. In some embodiments, $R_1$ is selected from $C_1$ to $C_4$ alkyl and alkenyl groups. In some embodiments, $R_1$ is selected from $C_1$ to $C_4$ alkyl groups. In some embodiments, $R_1$ is selected from $C_3$ to $C_4$ alkyl and alkenyl groups. In some embodiments, $R_1$ is selected from $C_3$ to $C_4$ alkyl groups. In some embodiments, the aldehyde is selected from formaldehyde, acetaldehyde, propionaldehyde, n-butyraldehyde, iso-butyraldehyde, n-pentanal (valeraldehyde), caproaldehyde, crotonaldehyde, n-heptaldehyde, n-octanal, n-nonylaldehyde, phenylacetaldehyde, benzaldehyde, p-tolualdehyde, salicylaldehyde, vanillin, piperonal, 2-ethyl-2-hex-enal and 2-ethylhexaldehyde. In some embodiments, the aldehyde is selected from formaldehyde, acetaldehyde, propionaldehyde, 2-ethyl-2-hex-enal, n-butyraldehyde, iso-butyraldehyde, n-pentanal (valeraldehyde), caproaldehyde, crotonaldehyde, n-heptaldehyde, n-octanal, n-nonylaldehyde and 2-ethylhexaldehyde. In some embodiments, the aldehyde is selected from formaldehyde, acetaldehyde, propionaldehyde, n-butyraldehyde, iso-butyraldehyde, n-pentanal (valeraldehyde), caproaldehyde, n-heptaldehyde, n-octanal, n-nonylaldehyde and 2-ethylhexaldehyde. In some embodiments, the aldehyde is selected from formaldehyde, acetaldehyde, propionaldehyde, n-butyraldehyde, iso-butyraldehyde, and 2-ethylhexaldehyde. In some embodiments, the aldehyde is selected from propionaldehyde, n-butyraldehyde, and iso-butyraldehyde. In some embodiments, the aldehyde is selected from acetaldehyde, propionaldehyde, n-butyraldehyde, and iso-butyraldehyde. In some embodiments, the aldehyde is selected from propionaldehyde, n-butyraldehyde, iso-butyraldehyde, and 2-ethylhexaldehyde. In some embodiments, the aldehyde is isobutyraldehyde. In some embodiments, the aldehyde is n-butyraldehyde. In some embodiments, the aldehyde is propionaldehyde. In some embodiments, the aldehyde is acetaldehyde. In some embodiments, the aldehyde is formaldehyde.

As used throughout this application, a "static mixer" shall mean a containment that is configured to allow flow through a lumen in the containment and that further possesses at least one internal structural element that is configured to promote mixing and/or dispersion of fluids that travel through the lumen in the containment. In some embodiments, a single structural element is used. In some embodiments, a plurality of structural elements is used.

Structural elements of the type above do not apply or add to the motive force but instead passively alter or direct flow of fluids that pass over or along them. In some embodiments, at least one internal structural element includes one or more constrictions positioned across the lumen and/or protuberances from the outer wall into the lumen that cause turbulence in the fluid flow. In some embodiments, the at least one internal structural element includes one or more baffles that aid in mixing. Some examples include baffles that divide flow, baffles that cause flowing material to experience rotational circulation, baffles that create turbulence, baffles that cause cross-stream mixing through blade intersections, and baffles that perform combinations of two or more of the foregoing. In some embodiments, a plurality of baffle is helically arranged around the axis of fluid flow in a series along the axis of fluid flow. In some embodiments, the series of helically arranged baffles are in a configuration that directs the flow of fluids radially toward the walls of the containment and back away from them that divide streams flowing through the stating mixer by alternating in directions between right-handed and left handed helices, or both. In some embodiments, the series of helically arranged baffles are in a configuration that divides the flow of fluids into two or more channels, causes rotational circulation of a processed material around its own hydraulic center in each channel, or both. In some embodiments, the baffles are arranged as low-profile tabs protruding into the lumen of the containment to induce turbulence. In some embodiments, the static mixture possesses one or more ports, injectors, nozzles or other openings that allow insertion of a material into the lumen during flow. Although static mixers are characterized by the presence of fixed internal structural elements that do not move and thus passively cause mixing, the term does not exclude devices outfitted with components that provide motive force (e.g. impellers) or moving parts in addition to the internal structural elements discussed above. Static mixers are available, for example from National Oilwell Varco, L.P. (Houston Tex.) and Koflo Corporation (Cary, Ill.).

Further Processing and Optional Recycling

The target product, isobutyric acid, can be recovered from a crude product composition or reaction mixture by any effective means. In each of the embodiments described above, the process can further include steps for separation and/or concentration of various constituents in the crude product composition or the reaction solution. Some examples of such constituents can include the product isobutyric acid, the carbonyl compound, unreacted isobutyraldehyde, isopropyl formate and non-IPF byproducts. Any effective or useful process or combination of processes for concentrating constituents can be used. Some examples include distillation, phase separation, extraction, decantation and membrane separation. In some embodiments, for example the crude product composition contains isobutyraldehyde and the process further includes processing at least some of the crude product composition in a manner that will concentrate at least some of the carbonyl compound in the crude product composition and at least some of the isobutyraldehyde in the crude product composition into a recycle composition and will concentrate at least some of the isobutyric acid in the crude product composition into an isobutyric acid product composition. Some or all of the recycle composition can then be fed back to the process i.e., to the reaction zone. Feeding the recycle composition to the reaction zone can include combining at least some of the recycle composition into the feed composition comprising isobutyraldehyde before feeding the feed composition comprising isobutyraldehyde to the reaction zone. Alternatively, the recycle composition may be combined with other compositions that are fed to the reaction zone, or fed separately to the reaction zone. These embodiments can allow for reuse of the carbonyl compound and convey unreacted isobutyraldehyde back to the process.

In embodiments in which the carbonyl compound is acetone, there is the additional benefit that acetone can form as a byproduct of isobutyraldehyde oxidation. This creates the opportunity for an additional benefit by from using byproduct that is already available. Acetone can thus derived from the crude product composition through downstream processes to concentrate acetone in the crude product composition to product a stream that is reused as co-feed with isobutyraldehyde such that the isobutyraldehyde/acetone mixtures listed above are utilized. It is advantageous to use the acetone by-product from the process because collected acetone eliminates the cost of purchasing fresh acetone. Furthermore, acetone is not foreign to the operating system/process/process and reuse removes or reduces the need to handle or to dispose of byproduct acetone.

In some embodiments, effective use of concentrating steps (such as distillation and decantation) can allow accumulation of sufficient carbonyl compound to satisfy the needs for carbonyl compounds under process of the invention, reducing or eliminating the need to add additional acetone to the process. The process can thus be part of an overall system that is self-satisfied as relates to carbonyl compound needs. Embodiments also exist in which the carbonyl compound is not reused or in which the carbonyl compound used in the process is a combination of fresh (unused) and recycled material.

In some embodiments, the reaction product of the uncatalyzed reaction may be run through a series of distillation columns such that isobutyraldehyde is recovered and recycled to the reactor. Non-selective products such as isopropyl formate can be separated, and purified isobutyric acid can be recovered. Decantation, evaporation, liquid-liquid extraction, or gas stripping can also be used in some embodiments to purify the isobutyric acid product and/or recover the carbonyl compound.

In some embodiments, the catalyzed process may likewise be run through a series of distillation columns such that carbonyl compound and unreacted isobutyraldehyde are recovered and recycled, isobutyric acid is recovered and purified, and the concentrated catalysts solution removed as a base heel and recycled to the reactor. In some embodiments, the catalyst may also be recovered by gas stripping the reactor solution to recover organics, water, and acids prior to distillation thus leaving a catalyst rich solution to be recycled to the reactor. Decantation, evaporation, or liquid-liquid extraction may also be useful in some embodiments for separation of reaction products and recovery of the catalyst solution.

This invention can be further illustrated by the following examples of preferred embodiments thereof, although it will be understood that these examples are included merely for purposes of illustration and are not intended to limit the scope of the invention unless otherwise specifically indicated.

EXAMPLES

Examples 1-10 were all carried out in a laboratory scale continuous oxidation reactor. The reactor was constructed of an eighteen inch long×1.5 inch diameter 316 stainless steel pipe. The bottom of the pipe was capped with a 0.25 inch outer diameter (O.D.) stainless steel tube, topped on one end with a stainless steel 15 micron diameter pore filter element The filter element had an open end and a closed end and was run through the cap with the closed end upward. Liquids were pumped into the column via a laboratory scale pump capable of feed rates up to 20 milliliters per minute (mL/min) and pressures up to 3000 psig. Air was supplied from a compressed gas cylinder and its flow rate controlled by means of a standard rotometer. The liquid and gas feed lines were joined at a "tee" before passing through the pores of the filter element into the reactor. Pressure in the reactor was controlled by means of back pressure regulator.

The reactor was wrapped in electrically heated tape and controlled by an electronic heater which monitors the skin temperature of the reactor via a J-type thermocouple. A "cold finger" comprised of a 0.5 inch O.D. stainless steel tube sealed at one end and filled with chilled glycol, ran from the top of the reactor to ¾ of the length of the pipe in the reaction mixture and was used to remove generated heat and control the internal temperature. The internal temperature was monitored by an internal K-type thermocouple connected to an electronic controller. The controller operated a solenoid valve which allowed glycol into the "finger" when the internal temperature exceeded a set point.

The top of the reactor was fitted with two "pipe tees" that allow for liquid and gas overflow. The liquid overflow passed through the first tee into a glycol chilled condenser and into a product tank. The gas overflow passed through the second tee, through the back pressure regulator. The gas overflow passed through three dry ice traps to collect more condensables. The liquid from these dry ice traps was combined with the liquid overflow and analyzed by gas chromatogram. The gas from the third ice trap was periodically sampled and analyzed by gas chromatography (GC) as well.

In a typical experiment, the reactor was filled with isobutyric acid and the appropriate weight % of acetone. The reactor was heated to an internal temperature of 40° C. under 55 psig. Upon reaching the desired internal temperature, a feed tank was charged with isobutyraldehyde and the desired weight % of acetone. The mixture was fed into the reactor at a rate of 1.5 mL/min. Air was fed into the reactor at a rate of 1 standard liters per minute (SLPM). The internal temperature was monitored and maintained at 40° C. The pressure was maintained at 55 psig. The liquid overflow was measured and weighed every hour and a sample analyzed by GC. The gas outlet was sampled and analyzed by GC periodically. A typical experiment lasts 7 hours.

All GC herein was performed pursuant to the follow procedure. Liquid GC samples were prepared by adding 0.3 grams of liquid overflow to an autosampler vial containing 1.0 grams of a 22.5% heptane/toluene solution. The sample was vigorously shaken and 1.0 microliters was injected on an HP 6890 gas chromatograph equipped with a Restek RTx-1701 column (Restek Corporation, Bellefont Pa.) (30.0 meters×320 microns×1.00 microns) and an flame ionization (FID) detector. The initial temperature of the oven was 50° C. and the temperature was ramped to 150° C. with an increase of 10° C. every minute with a hold time of 5.00 minutes. The total time of the analysis was 17.00 minutes. The concentration of analytes was determined based on response times of prepared standards relative to heptane as an internal standard.

Gas GC samples were collected in a 0.5 liter TEDLAR sampling bag (also available from Restek Corporation). The gas mixture was injected on an HP 6890 gas chromatograph equipped with a sample loop that holds approximately 14000 nanomoles of gas and a thermal conductivity detector. The gas was separated on an Agilent HP-PLOTQ (available from Agilent Technologies, Santa Clara, Calif.) column (25.0 meters×320 microns×10.00 microns). The column was maintained at 15 psig with an average velocity of 55 centimeters per second. The initial temperature of the instrument oven was 50° C. with a 4 minute hold time. The oven was heated at 25° C. per minute with a hold time of 15 minutes to a final temperature of 220° C. Total elution takes 25.80 minutes. Concentrations of analytes were determined by comparing to retention times and response factors from a known mixture of gases. Residence time was calculated for Examples 1-10 at less than one minute.

Comparative Example 1

Control, Oxidation of iHBu with 0% Acetone

The reactor was charged with 540 milliliters (mL), which was 524 grams (g) of isobutyric acid. After heating to 40° C. under 55 psig, iHBu was fed into the reactor at 1.5 mL/min. Air was fed into the reactor at 1 SLPM. Liquid overflow and gas effluent was collected, weighed, and analyzed by gas chromatography (GC) hourly. After 7 hours, the feeds were ceased, gas was vented, and the reactor was cooled, emptied, and its contents weighed and analyzed. The overflow was found to contain, by mass %, 91.0% isobutyric acid, 3.96% IPF, 2.48% acetone, 1.48% iHBu, 0.97% carbon dioxide ($CO_2$) and 0.11% isopropanol.

Example 2

Oxidation of iHBu with 5% Acetone

The reactor was charged with 540 mL of 95% isobutyric acid and 5% acetone. After heating to 40° C. under 55 psig, a mixture of 95% iHBu and 5% acetone was fed into the reactor at 1.5 mL/min. Air was fed into the reactor at 1 SLPM. Liquid overflow and gas effluent was collected, weighed, and analyzed by GC hourly. After 7 hours, the feeds were ceased, gas was vented, and the reactor was cooled, emptied, and its contents weighed and analyzed. The overflow was found to contain 86.0% isobutyric acid, 2.25% IPF, 8.72% acetone, 2.45% iHBu, 0.55% $CO_2$, and 0.0% isopropanol.

Example 3

Oxidation of iHBu with 10% Acetone

The reactor was charged with 540 mL of 90% isobutyric acid and 10% acetone. After heating to 40° C. under 55 psig, a mixture of 90% iHBu and 10% acetone was fed into the reactor at 1.5 mL/min. Air was fed into the reactor at 1 SLPM. Liquid overflow and gas effluent was collected, weighed, and analyzed by GC hourly. After 7 hours, the feeds were ceased, gas was vented, and the reactor was cooled, emptied, and its contents weighed and analyzed. The overflow was found to contain 79.5% isobutyric acid, 2.28% IPF, 14.71% acetone, 2.98% iHBu, 0.53% $CO_2$, and 0.0% isopropanol.

Example 4

Oxidation of iHBu with 25% Acetone

The reactor was charged with 540 mL of 75% isobutyric acid and 25% acetone. After heating to 40° C. under 55 psig, a mixture of 75% iHBu and 25% acetone was fed into the reactor at 1.5 mL/min. Air was fed into the reactor at 1 SLPM. Liquid overflow and gas effluent was collected, weighed, and analyzed by GC hourly. After 7 hours, the feeds were ceased, gas was vented, and the reactor was cooled, emptied, and its contents weighed and analyzed. The overflow was found to contain 72.7% isobutyric acid, 1.34% IPF, 23.5% acetone, 2.10% iHBu, 0.37% $CO_2$, and 0.02% isopropanol.

Example 5

Oxidation of iHBu with 50% Acetone

The reactor was charged with 540 mL of 50% isobutyric acid and 50% acetone. After heating to 40° C. under 55 psig, a mixture of 50% iHBu and 50% acetone was fed into the reactor at 1.5 mL/min. Air was fed into the reactor at 1 SLPM. Liquid overflow and gas effluent was collected, weighed, and analyzed by GC hourly. After 7 hours, the feeds were ceased, gas was vented, and the reactor was cooled, emptied, and its contents weighed and analyzed. The overflow was found to contain 53.4% isobutyric acid, 0.19% IPF, 45.8% acetone, 0.49% iHBu, 0.22% $CO_2$, and 0.00% isopropanol.

TABLE 1

| Ex | Acetone | iHBu Conversion | iHOBu Selectivity | iHOBu Yield | IPF Selectivity | Wt % IPF | Other Byproduct Selectivity | STY (g acid/ L *s) | Reduced IPF |
| --- | --- | --- | --- | --- | --- | --- | --- | --- | --- |
| C1 | 0% | 96% | 82% | 81% | 7.2% | 4.0% | 10% | 1.6 | 0% |
| 2 | 5% | 96% | 85% | 85% | 5.1% | 2.3% | 9.5% | 1.5 | 43% |
| 3 | 10% | 92% | 86% | 86% | 6.4% | 2.3% | 8.0% | 1.5 | 42% |
| 4 | 25% | 94% | 86% | 81% | 6.1% | 1.3% | 5.3% | 1.5 | 66% |
| 5 | 50% | 96% | 97% | 95% | 1.7% | 0.19% | 3.2% | 0.93 | 95.3% |

Table 1 shows the increase in selectivity and yield of isobutyric acid (based on mol %) as the weight % of acetone was increased from 0% to 50%. The Table also shows the decrease in selectivity to IPF and other by-products ($CO_2$, propylene, propane, acetone, and isopropanol). At 50%, the space time yield (STY) falls to levels that counteract the benefits of increased yield.

Comparative Example 6

Oxidation of 2-ethylhexanal

The oxidation reactor described above was charged with 500 mL of 2-ethylhexanoic acid. The reactor was heated to 40° C. under 55 psig of air. 2-ethylhexanal was fed at 1.0 mL/min and purified air at 1000 SCCM. The reactor effluent was collected, weighed, and analyzed each hour. The overflow was comprised of 85.9% acid, 7.94% 2-ethylhexanal, 4.27% heptyl formate (HPF), 0.83% 3-heptanone, 0.94% 3-heptanol, 0.12% heptane, and 0% acetone.

Comparative Example 7

Oxidation of 2-ethylhexanal with 10% Acetone

The oxidation reactor described above was charged with 500 mL of 90% 2-ethylhexanoic acid and 10% acetone. The reactor was heated to 40° C. under 55 psig of air. A mixture of 90% 2-ethylhexanal and 10% acetone was fed at 1.0 mL/min and purified air at 1000 SCCM. The reactor effluent was collected, weighed, and analyzed each hour. The overflow was comprised of 73.1% acid, 5.59% 2-ethylhexanal, 10.8% heptyl formate, 1.20% 3-heptanone, 0.72% 3-heptanol, 0.18% heptane, and 8.41% acetone.

Comparative Example 8

Oxidation of 2-ethylhexanal with 25% Acetone

The oxidation reactor described above was charged with 500 mL of 75% 2-ethylhexanoic acid and 25% acetone. The reactor was heated to 40° C. under 55 psig of air. A mixture of 75% 2-ethylhexanal and 25% acetone was fed at 1.0 mL/min and purified air at 1000 SCCM. The reactor effluent was collected, weighed, and analyzed each hour. The overflow was comprised of 58.2% acid, 2.52% 2-ethylhexanal, 14.1% heptyl formate, 1.80% 3-heptanone, 0.80% 3-heptanol, 0.22% heptane, and 22.3% acetone.

TABLE 2

| Example | % Acetone | 2-ethylhexanal Conversion | 2-ethylhexanoic Acid Selectivity | % HPF | % Other byproducts |
| --- | --- | --- | --- | --- | --- |
| 6 | 0% | 92.0% | 88.7% | 4.27% | 7.00% |
| 7 | 10% | 93.2% | 75.1% | 10.8% | 14.1% |
| 8 | 25% | 96.9% | 64.6% | 14.1% | 21.3% |

Comparative Examples 6-8 are summarized in Table 2. Table 2 indicates that the use of acetone does not appear to reduce the HPF byproduct in a similar process of making 2-ethylhexanoic acid. In fact, it increased the HPF byproduct by more than 100%. As the concentration of acetone increases in the feed, the selectivity to 2-ethylhexanoic acid decreases and the concentration of heptyl formate increases.

Example 9

Oxidation of Isobutyraldehyde with 10% Ethyl Acetate

The oxidation reactor described above was charged with 540 mL of 90% isobutyric acid and 10% ethyl acetate. The reactor was heated to 40° C. under 55 psig of air. A mixture of 90% isobutyraldehyde and 10% ethyl acetate was fed at 1.0 mL/min and purified air at 1000 SCCM. The reactor effluent was collected, weighed, and analyzed each hour. The overflow was comprised of 89.8% isobutyric acid, 6.66% ethyl acetate, 1.81% isopropyl formate, 0.88% acetone, 0.80% iHBu, 0.04% $CO_2$.

Example 10

Oxidation of Isobutyraldehyde with 25% Ethyl Acetate

The oxidation reactor described above was charged with 540 mL of 75% isobutyric acid and 25% ethyl acetate. The reactor was heated to 40° C. under 55 psig of air. A mixture of 75% isobutyraldehyde and 25% ethyl acetate was fed at 1.0 mL/min and purified air at 1000 SCCM. The reactor effluent was collected, weighed, and analyzed each hour. The overflow was comprised of 78.7% isobutyric acid, 17.2% ethyl acetate, 2.12% isopropyl formate, 0.30% acetone, 1.67% iHBu, 0.04% $CO_2$.

TABLE 3

| Example | % ethyl acetate | iHBu Conversion | iHOBu Selectivity | iHOBu Yield | wt % IPF | Selectivity to other Byproducts |
| --- | --- | --- | --- | --- | --- | --- |
| 1 | 0% | 96.2% | 82.4% | 81.1% | 3.96% | 10.4% |
| 9 | 10% | 97.5% | 84.6% | 82.3% | 1.81% | 4.85% |
| 10 | 25% | 95.6% | 83.9% | 78.8% | 2.12% | 2.51% |

The results in Table 3 show that the use of ethyl acetate as the carbonyl compound can also reduce the IPF byproduct, although to a lesser degree than acetone.

Example 11

Oxidation in a Static Mixer

Four streams are combined at the piping immediately before the entrance of the reactor. The streams are: a raw material liquid stream containing at least 98 weight percent isobutyraldehyde at a rate of 1-2 volumetric parts per minute; compressed air (125 psig) at a rate of 300-1500 volumetric parts per minute, liquid recycle from the top of the second distillation column (described below) at 0.5 to 1 volumetric parts per min, and a scrubber recycle stream (described below) fed at 24-60 volumetric parts per minute. The reaction zone is a KENICS KM-type mixer available from National Oilwell Varco, L.P. (Houston Tex.). Material is fed to the reactor at an inlet pressure ranging from 90-125 psig and a temperature ranging from about 40 to 60 degrees C. The mixer is a cylindrical tube having an internal volume of 0.4 volumetric parts and 38 helical internal baffles that divide the flow in alternating right and left hand helices The resulting crude product composition is subjected to a series of distillation processes to concentrate isobutyric acid in a refined product composition by removing or reducing levels of isobutyraldehyde, IPF and other byproducts from the stream. The crude product composition is first fed to a flash tank (10-30 psig and 40 C) where the liquid primary product stream accumulates at a rate of 25-62 volumetric parts per minute and gasses are vented at a rate of 240-1200 volumetric parts per minute. Both of these streams are sent to a scrubber that contains three beds of random packing (10-30 psig and 40 C).

In the scrubber, the gas stream is scrubbed with chilled (5-20° C.) isobutyric acid (at a rate of 0.6-1.2 volumetric parts per minute) to separate the liquid stream containing isobutyric acid and other impurities and an off gas stream containing unreacted oxygen, nitrogen, and other residual carbon compounds. The off gas stream is removed from the scrubber and leaves the process. The liquid stream is split into two with a portion that is cooled in heat exchangers to remove the heat of reaction and recycled to the feed to the reaction zone (scrubber recycle stream mentioned above) and the remainder that is sent to an intermediate storage tank.

The liquid primary product stream from the intermediate storage tank is fed to a distillation column (4 beds of structured packing (40 theoretical stages) at a combined rate of 2.1-4.2 volumetric parts per minute. The base conditions are 3 psig and 161 C with a top pressure around atmospheric pressure and 63 C. The reflux ratio ranges from 1-1.5. The distillation column concentrates isobutyric acid as a final product in an underflow stream (70% of feed) and various lower boiling impurities (e.g., acetone, unreacted isobutyraldehyde, isopropyl formate, and water) in an overhead stream (30% of feed).

The overhead stream is condensed and then fed to a decanter. Water is added to the decanter to produce an organic and aqueous phase. The amount of water varies based on the acid content of the organic phase. The aqueous phase containing mostly water and acetone is sent off as a waste purge stream, while the organic phase containing isobutyraldehyde, isopropyl formate, and acetone is routed back to the distillation column as reflux. Optionally, part of the organic phase is partially routed to a second distillation column which is packed with 3 beds of structured packing (23 theoretical stages). The base conditions are 6 psig and 81 C with a top column pressure around 5 psig and temperature of 71 C. The reflux ratio ranges from 1-1.5. The second column produces an overhead stream containing unreacted isobutyraldehyde and acetone and an underflow stream of isopropyl formate. The isobutyraldehyde and acetone can be used as part of the initial feedstock for the system.

The procedure above is repeated except that the raw material liquid stream fed to the reactor is blended with acetone prior to being combined with the compressed air. The amount of acetone added is such that the resulting liquid stream from the reaction zone has an acetone content of about 15% by weight. This procedure is repeated while varying the acetone content between about 5 and about 25% by weight.

The procedure described in the preceding paragraph is repeated except that the acetone used is byproduct acetone that is obtained from a byproduct composition. This is accomplished by reducing the amount of water used in the phase separation discussed above so that a greater amount of acetone remains in the organic phase, then recycling the organic phase for use in the feed to the reaction zone.

Each of the above procedures are repeated while varying pressure and temperature of the liquid feed to the is varied in a range from 90 to 125 psig and a temperature ranging from about 40 to about 60 degrees C. Residence time was 5 minutes or less.

Example 12

Oxidation in a Bubble Column

Example 11 and all variants thereof are repeated using a different equipment configuration. A bubble column reactor with internal cooling coils to remove the heat of reaction and a sieve tray at the bottom of the reactor to distribute the air can be utilized instead of a static mixer as the reactor. The initial temperature of the liquid feed to the reactor is 30-60 degrees C. and the pressure range is 30 to 60 psig. The bubble column design does not use a recycle loop from the scrubber. The raw material liquid stream containing at least 98 weight percent isobutyraldehyde is fed at a rate of 14-22 volumetric parts per minute and compressed air (75 psig) is fed at a rate of 9624-15,200 volumetric parts per minute. A recycle stream (14 volumetric parts per minute) from the top of the second column (discussed below) containing the aldehyde, optionally some acetone, and some IPF is also mixed into the reaction feed. Residence time in the bubble column reactor is less than 120 minutes. The resulting crude product composition from the bottom of the bubble column is subjected to a series of distillation processes to concentrate isobutyric acid in a refined product composition by removing or reducing levels of isobutyraldehyde, IPF and other byproducts from the stream.

The gas stream from the top of the bubble column crude is vented at a rate of 7700-12,160 volumetric parts per minute to a scrubber that contains structured packing (50-55 psig and 5° C.). In the scrubber, the gas stream is scrubbed with chilled (15-35° C.) isobutyric acid (at a rate of 8-14 volumetric parts per minute) to separate the gaseous stream into a secondary product stream containing isobutyric acid and other impurities and an off gas stream containing unreacted oxygen, nitrogen, and other residual carbon compounds. The off gas stream is removed from the scrubber and ultimately sent to a catalytic oxidizer, while the secondary product stream is combined with the crude product composition before introduction into a distillation column.

The crude product composition and the secondary product stream are fed to a distillation column (40 sieve trays) at a combined rate of 28-54 volumetric parts per minute. This combination occurs either by feeding the liquid primary product stream to a lower portion of the scrubber or by piping together the primary product stream and secondary product stream downstream of the scrubber, or feeding both streams to a distillation column. The distillation column concentrates isobutyric acid as a final product in an underflow stream or vapor takeoff near bottom of column. The rest of the column conditions are described above.

The overhead stream is condensed and then fed to a decanter. Water is added to the decanter to produce an organic and aqueous phase. The amount of water varies based on the acid content of the organic phase. The aqueous phase containing mostly water and acetone is sent off as a waste purge stream, while the organic phase containing isobutyraldehyde, isopropyl formate, and acetone is routed back to the distillation column as reflux. Optionally, part of the organic phase is partially routed to a second distillation column which is packed with structured packing. The rest of the column details were described previously. The second column produces an overhead stream containing unreacted isobutyraldehyde and acetone and an underflow stream of isopropyl formate. The isobutyraldehyde and acetone can be used as part of the initial feedstock for the system.

Each of the above procedures are repeated while varying pressure and temperature of the liquid feed to the is varied in a range between from 30 to 60 psig and a temperature ranging from about 30 to about 60 degrees C.

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

The invention claimed is:

1. A method for reducing isopropyl formate in a process of producing Isobutyric acid comprising contacting two or more Isobutyraldehyde compositions, a solvent selected from acetone and ethyl acetate, a co-solvent, and a catalyst selected from the group consisting of a salt of a noble metal, a salt of a transition metal, a salt of cobalt, a salt of chromium, or a salt of manganese in the presence of an oxidant to form Isobutyric acid, wherein the formation of isopropyl formate is reduced by weight compared with the production of Isobutyric acid in the absence of a co-solvent.

2. The method of claim 1 wherein the co-solvent comprises a carbonyl compound.

3. A method for reducing isopropyl formate in a process of producing Isobutyric acid, in a plug flow reactor, comprising contacting two or more Isobutyraldehyde compositions, a solvent selected from acetone and ethyl acetate, a co-solvent, and a catalyst selected from the group consisting of a salt of a noble metal, a salt of a transition metal, a salt of cobalt, a salt of chromium, or a salt of manganese in the presence of an oxidant to form Isobutyric acid, wherein the formation of isopropyl formate is reduced by weight compared with the production of Isobutyric acid in the absence of a co-solvent.

4. The method of claim 3 wherein the co-solvent comprises a carbonyl compound.

5. A method for reducing isopropyl formate in a process of producing Isobutyric acid comprising contacting two or more Isobutyraldehyde compositions, a solvent selected from acetone and ethyl acetate, and acetone in the presence of an oxidant to form isobutyric acid, wherein the formation of isopropyl formate is reduced by weight compared with production of Isobutyric acid in the absence of a co-solvent, wherein at least some of the acetone is a byproduct collected from the process and at least some of the acetone is freshly added.

6. The method of claim 5 wherein, the formation of isopropyl formate is reduced by 20% to 50% by weight.

7. The method of claim 5 wherein, the formation of isopropyl formate is reduced by 50% to 80% by weight.

8. The method of claim 5 wherein, the formation of isopropyl formate is reduced by 80% to 95.5% by weight.

9. The method of claim 5 wherein, the formation of isopropyl formate is reduced by at least 95.5% by weight.

* * * * *